United States Patent
Borneo et al.

(10) Patent No.: US 12,174,166 B2
(45) Date of Patent: Dec. 24, 2024

(54) ASSIGNMENT AND DE-ASSIGNMENT IN PORTABLE DEVICES VIA A CHARGER

(71) Applicant: MSA TECHNOLOGY, LLC, Cranberry Township, PA (US)

(72) Inventors: Chris Borneo, Pittsburgh, PA (US); Steve Denninger, Pittsburgh, PA (US); Victor Lejeune, Bishop's Waltham (GB)

(73) Assignee: MSA Technology, LLC, Cranberry Township, PA (US)

( * ) Notice: Subject to any disclaimer, the term of this patent is extended or adjusted under 35 U.S.C. 154(b) by 490 days.

(21) Appl. No.: 17/496,420

(22) Filed: Oct. 7, 2021

(65) Prior Publication Data

US 2023/0113553 A1  Apr. 13, 2023

(51) Int. Cl.
*G01N 33/00* (2006.01)
*G06K 7/10* (2006.01)
(Continued)

(52) U.S. Cl.
CPC ..... *G01N 33/0027* (2013.01); *G01N 33/0075* (2013.01); *G06K 7/10366* (2013.01);
(Continued)

(58) Field of Classification Search
CPC ........... G01N 33/0027; G01N 33/0075; G01N 33/0009; G01N 33/0073; G06K 7/10366;
(Continued)

(56) References Cited

U.S. PATENT DOCUMENTS 6,182,497 B1 * 2/2001 Krajci ............ H04Q 9/00
73/40.5 R
6,442,639 B1 * 8/2002 McElhattan ........ G16H 40/67
710/305

(Continued)

FOREIGN PATENT DOCUMENTS

EP 2490193 B1 1/2014
EP 2770967 B1 5/2020
(Continued)

OTHER PUBLICATIONS

Specification Sheet, iAssign technology, Industrial Scientific Corporation, https://www.indsci.com/en/gas-detectors/technology1/iassign/ 2021.

(Continued)

*Primary Examiner* — Helen C Kwok
(74) *Attorney, Agent, or Firm* — BARTONY & ASSOCIATES LLC

(57) ABSTRACT

A management system includes a processor system in operative connection with a communication system. The communication system is configured to be in communicative connection with a gas monitoring system of an entity. The gas monitoring system further includes one or more portable gas detection instruments which include one or more gas sensors and a rechargeable battery system. The gas monitoring system further includes one or more chargers configured to charge the rechargeable battery system of each of the portable gas detection instruments. The management system further includes a memory system in operative connection with the processor system. The memory system includes an algorithm executable by the processor system stored therein and a database associated with the algorithm stored therein, which includes data identifying each of the chargers as an (Continued)

asset of the entity and each of the portable gas detection instruments as an asset of the entity.

17 Claims, 5 Drawing Sheets

(51) Int. Cl.
    *G06K 19/07*         (2006.01)
    *H02J 7/00*          (2006.01)

(52) U.S. Cl.
    CPC ...... *G06K 19/0723* (2013.01); *H02J 7/00032* (2020.01); *H02J 7/0013* (2013.01); *H02J 7/0044* (2013.01); *G01N 33/0009* (2013.01); *G01N 33/0073* (2013.01)

(58) Field of Classification Search
    CPC .............. G06K 19/0723; H02J 7/00032; H02J 7/0013; H02J 7/0044
    See application file for complete search history.

(56) References Cited

U.S. PATENT DOCUMENTS

| | | |
|---|---|---|
| 7,530,255 B2 | 5/2009 | Frank |
| 8,215,150 B2 | 7/2012 | Willett |
| 9,245,435 B2 | 1/2016 | Boone |
| 9,410,940 B2 | 8/2016 | Scheffler |
| 9,528,957 B2 | 12/2016 | Scheffler |
| 9,562,873 B2 | 2/2017 | Scheffler |
| 9,784,755 B2 | 10/2017 | Scheffler |
| 10,088,550 B2 | 10/2018 | Johnson |
| 10,368,146 B2 | 7/2019 | Potyrailo |
| 10,429,330 B2 | 10/2019 | Le Neel |
| 10,557,838 B2 | 2/2020 | Worth |
| 10,578,573 B2 | 3/2020 | Zanella, Sr. |
| 10,627,379 B2 | 4/2020 | Zanella, Sr. |
| 10,725,003 B2 | 7/2020 | Johnson |
| 10,782,274 B2 | 9/2020 | Worth |
| 10,788,457 B2 | 9/2020 | Miller |
| 10,788,458 B2 | 9/2020 | Miller |
| 10,948,469 B2 | 3/2021 | Zanella, Sr. |
| 10,983,103 B2 | 4/2021 | Stokoe |
| 2008/0117066 A1* | 5/2008 | Kononov ........... G01N 33/0009 340/632 |
| 2010/0081411 A1* | 4/2010 | Montenero ........ G01N 33/0075 455/404.2 |
| 2010/0212395 A1* | 8/2010 | Willett ............... G01N 33/0073 702/182 |
| 2010/0225493 A1* | 9/2010 | Zishaan ................... F24F 11/30 340/627 |
| 2011/0037599 A1* | 2/2011 | Johnson, Jr. .......... H04W 4/023 340/632 |
| 2012/0191349 A1* | 7/2012 | Lenz .................. G01N 33/0075 702/2 |
| 2012/0212347 A1* | 8/2012 | Boone .................... G08B 21/12 340/632 |
| 2017/0047748 A1* | 2/2017 | Blyde .................... H02J 7/0049 |
| 2019/0064132 A1 | 2/2019 | Poecher |
| 2019/0349360 A1 | 11/2019 | Yeddula |
| 2020/0058963 A1* | 2/2020 | Morris ................ H02J 7/00034 |
| 2020/0090297 A1 | 3/2020 | Fabes |
| 2020/0103387 A1 | 4/2020 | Brown |
| 2020/0363306 A1 | 11/2020 | Sexton |
| 2020/0393405 A1 | 12/2020 | Scheffler |
| 2021/0181135 A1 | 6/2021 | Santoro, Jr. |

FOREIGN PATENT DOCUMENTS

| | | | |
|---|---|---|---|
| WO | WO2015065390 A1 | 5/2015 | |
| WO | WO2019152047 A1 | 8/2019 | |
| WO | WO2020225796 A1 | 11/2020 | |

OTHER PUBLICATIONS

Sheet Using the Venti Pro Series with iAssign Technology, Industrial Scientific Corporation, https://www.indsci.com/en/gas-detectors/technology1/iassign/ 2021.

Star-Up Guide, https://www.indsci.com/en/gas-detectors/technology1/iassign/, Edition 3, Mar. 26, 2021.

* cited by examiner

ASSIGNMENT AND DE-ASSIGNMENT IN PORTABLE DEVICES VIA A CHARGER

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Gas detection devices (commonly referred to as "instruments") include at least one gas sensor, electronic circuitry, and a power supply to drive the sensor, interpret its response, and display its response to the user. Such gas detection instruments may include a variety of sensors for detecting gas analytes including, for example, electrochemical gas sensors and combustible gas sensors. See, for example, U.S. Pat. No. 9,784,755, the disclosure of which is incorporated herein by reference. Gas detection instruments further include a housing to enclose and protect such components. Gas detection instruments may be portable or fixed in position. Portable gas detection instruments are typically powered by a rechargeable battery system. Portable gas detection instruments are carried on the person of an authorized user or worker within a company/facility that may own or rent the portable gas detection instrument as an asset of the facility. Depending upon size and industry, a company/facility may, for example, have several, tens, or hundreds or more of such instruments that are shared amongst a large, dynamic, and transitory workforce.

The tracking, maintaining, and controlling of portable gas detection instruments and accessories thereof can become cumbersome and complex, particularly in large facilities. As part of tracking portable gas detections instruments, at the start of a work shift, an authorized user goes through a procedure to assign a portable gas detection instrument. Likewise, at the end of the shift, the authorized user returns the portable gas detection instruments and goes through a return procedure. Under current practices, such procedures are typically recorded on paper or manually entered into a dedicated software program that is separate from other tracking, maintenance, and/or control procedures and processes.

SUMMARY

In one aspect, a management system includes a processor system and a communication system in operative connection with the processor system. The communication system is configured to be in communicative connection with a gas monitoring system of an entity. The gas monitoring system further includes one or more portable gas detection instruments. Each of the portable gas detection instruments includes one or more gas sensors and a rechargeable battery system. The gas monitoring system further includes one or more chargers configured to charge the rechargeable battery system of each of the portable gas detection instruments. The management system further includes a memory system in operative connection with the processor system. The memory system includes an algorithm executable by the processor system stored therein and a database associated with the algorithm stored therein. The database includes data identifying each of the chargers as an asset of the entity and each of the portable gas detection instruments as an asset of the entity.

Upon docking of one of the portable gas detection instruments with one of the chargers, communication between the one of the portable gas detection instruments which is docked and the one of the chargers is initiated and data is communicated to the management system electronically by the gas monitoring system regarding the docking and an identity of the one of the chargers. The processor system of the management system is configured, upon communication of the data regarding the docking and an identity of the one of the chargers from the gas monitoring system to the management system, to execute the algorithm to confirm identification of the one of the chargers as an asset of the entity, and to de-assign the one of the portable gas detection instruments from one of a plurality of users to whom the gas detection instrument was previously assigned if one of the chargers is determined to be an asset of the entity.

In a number of embodiments, the gas monitoring system further includes a plurality of identifying communication devices. Each of the plurality of identifying communication devices is configured to be associated with one of the plurality of users and to be carried on the person of the one of the plurality of users. The database further include data identifying the one of the plurality of users associated with each of the plurality of identifying communication devices. Upon removal of the portable gas detection instrument from one of the chargers by one of the plurality of users and positioning of the one of the plurality of identifying communication devices associated with the one of the plurality of users in proximity with portable gas detection instrument, communication between the one of the portable gas detections instruments and the one of the plurality of identifying communication devices associated with the one of the plurality of users is initiated and data regarding the identity of one of the portable gas detection instrument and identity of the one of the plurality of users is communicated to the management system electronically by the gas monitoring system. The processor system of the management system is configured, upon communication of the data regarding the identity of one of the portable gas detection instrument and identity of the one of the plurality of user from the gas monitoring system to the management system, to execute the algorithm to assign the one of the gas detection instruments to the one of the plurality of users.

In a number of embodiments, each of the portable gas detection instruments includes electronic circuitry in operative connection with the rechargeable battery system, a communication system in operative connection with the electronic circuitry, and a communication device in operative connection with the electronic circuitry. Each of the chargers may, for example, include one or more charging bays to recharge the rechargeable battery system of the portable gas detection instruments. Each of the chargers may further include a separate cooperating communication device associated with each one of the one or more charging bays which is unique to the charger and is configured to communicate information to the communication device of the portable gas detection instrument when the portable gas detection instrument is docked in the associated one of the one or more charging bays.

Data may, for example, be communicated to the management system from the gas monitoring system via the communication system of the portable gas detection instruments. In a number of embodiments, the communication system of each of the portable gas detection instruments communicates with the management system via cellular connectivity. The communication device of each of the portable gas detection instruments in a number of embodiments includes an RFID reader, the cooperating communication device of each of the chargers comprises an RFID tag, and each of the plurality of identifying communication devices comprises and RFID tag.

In a number of embodiments, data transmitted to the management system by the one of the portable gas detection instruments assigned to the one of the plurality of users regarding use of the one of the portable gas detection instruments is associated to the one of the plurality of users until the one of the portable gas detection instrument is de-assigned from the one of the plurality of users by the management system.

In another aspect, a method of managing a gas monitoring system of an entity, which includes one or more portable gas detection instruments, wherein each portable gas detection instrument includes one or more gas sensors and a rechargeable battery system, and one or more chargers configured to charge the rechargeable battery system of each of the portable gas detection instruments, includes placing a management system in communicative connection with the gas monitoring system. The management system includes a processor system, a communication system in operative connection with the processor system and configured to be placed in communicative connection with a gas monitoring system of the entity, and a memory system in operative connection with the processor system. The memory system includes an algorithm executable by the processor system stored therein and a database associated with the algorithm stored therein. The database includes data identifying each of the chargers as an asset of the entity and each of the portable gas detection instruments as an asset of the entity. Upon docking of one of the portable gas detection instruments with one of the chargers, communication is initiated between the portable gas detection instrument docked and the one of the chargers. The method further includes communicating data from the gas monitoring system to the management system regarding the docking and an identity of the one of the chargers. Further, upon communication of the data regarding the docking and an identity of the one of the chargers from the gas monitoring system to the management system, the processor system executes the algorithm to confirm identification of the one of the chargers as an asset of the entity and to de-assign the one of the portable gas detection instruments from one of a plurality of users to whom the gas detection instrument was previously assigned if one of the chargers is determined to be an asset of the entity.

The gas monitoring system may, for example, further includes a plurality of identifying communication devices, wherein each of the plurality of identifying communication devices is configured to be associated with one of the plurality of users and to be carried on the person of the one of the plurality of users. The database may further include data identifying the one of the plurality of users associated with each of the identifying communication devices, wherein, upon removal of the portable gas detection instrument from one of the chargers by one of the plurality of users and positioning of the one of the plurality of identifying communication devices associated with the one of the plurality of users in proximity with portable gas detection instrument, communication between the one of the portable gas detections instruments and the one of the plurality of identifying communication devices associated with the one of the plurality of users is initiated and data regarding the identity of one of the portable gas detection instrument and identity of the one of the plurality of users is communicated to the management system electronically by the gas monitoring system. The processor system of the management system may, for example, be configured, upon communication of the data regarding the identity of one of the portable gas detection instrument and identity of the one of the plurality of user from the gas monitoring system to the management system, to execute the algorithm to assign the one of the gas detection instruments to the one of a plurality of users.

In a number of embodiments, each of the portable gas detection instruments includes electronic circuitry in operative connection with the rechargeable battery system, a communication system in operative connection with the electronic circuitry, and a communication device in operative connection with the electronic circuitry. Each of the chargers may, for example, include one or more charging bays to recharge the rechargeable battery system of the portable gas detection instruments. Each of the chargers may, for example, include a separate cooperating communication device associated with each one of the one or more charging bays which is unique to the charger and is configured to communicate information to the communication device of the portable gas detection instrument when the portable gas detection instrument is docked in the associated one of the one or more charging bays.

In a number of embodiments, data is communicated to the management system from the gas monitoring system via the communication system of the portable gas detection instruments. The communication system of each of the portable gas detection instruments may, for example, communicate with the management system via cellular connectivity. In a number of embodiments, the communication device of each of the portable gas detection instruments include an RFID reader, the cooperating communication device of each of the chargers includes an RFID tag, and each of the plurality of identifying communication devices includes an RFID tag.

Data transmitted to the management system by the one of the portable gas detection instruments assigned to the one of the plurality of users regarding use of the one of the portable gas detection instruments may, for example, be associated to the one of the plurality of users until the one of the portable gas detection instrument is de-assigned from the one of the plurality of users by the management system.

In another aspect, a system includes a gas monitoring system of an entity and a management system. The gas monitoring system of the entity include one or more portable gas detection instruments, wherein each portable gas detection instrument include one or more gas sensors and a rechargeable battery system, and one or more chargers configured to charge the rechargeable battery system of each of the portable gas detection instruments. The management system includes a processor system, a communication system configured to be in communicative connection with a gas monitoring system of the entity, and a memory system in operative connection with the processor system. The memory system includes an algorithm executable by the processor system stored therein and a database associated with the algorithm stored therein. The database includes data identifying each of the chargers as an asset of an entity and each of the portable gas detection instruments as an asset of the entity. Upon docking of one of the portable gas detection instruments with one of the chargers, communication between the portable gas detection instrument docked and the one of the chargers is initiated and data is communicated to the management system electronically by the gas monitoring system regarding the docking and an identity of the one of the chargers. The processor system of the management system may be configured, upon communication of the data regarding the docking and an identity of the one of the chargers from the gas monitoring system to the management system, to execute the algorithm to confirm identification of the one of the chargers as an asset of the entity, and to de-assign the one of the portable gas detection instruments from one of a plurality of users to whom the gas detection instrument was previously assigned if one of the chargers is determined to be an asset of the entity.

In a number of embodiments, the gas monitoring system further includes a plurality of identifying communication devices, wherein each of the plurality of identifying communication devices is configured to be associated with one of the plurality of users and to be carried on the person of the one of the plurality of users. The database may, for example, further include data identifying the one of the plurality of users associated with each of the plurality of identifying communication devices. Upon removal of the portable gas detection instrument from one of the chargers by one of the plurality of users, positioning of the one of the plurality of identifying communication devices associated with the one of the plurality of users in proximity with portable gas detection instrument, initiates communication between the one of the portable gas detections instruments and the one of the plurality of identifying communication devices associated with the one of the plurality of users. Further, data regarding the identity of one of the portable gas detection instrument and identity of the one of the plurality of users is communicated to the management system electronically by the gas monitoring system. The processor system of the management system is configured, upon communication of the data regarding the identity of one of the portable gas detection instrument and identity of the one of the plurality of user from the gas monitoring system to the management system, to execute the algorithm to assign the one of the gas detection instruments to the one of a plurality of users.

In a number of embodiments, each of the portable gas detection instruments includes electronic circuitry in operative connection with the rechargeable battery system, a communication system in operative connection with the electronic circuitry, and a communication device in operative connection with the electronic circuitry. Each of the chargers may, for example, include one or more charging bays to recharge the rechargeable battery system of the portable gas detection instruments. Each of the chargers may include a separate cooperating communication device associated with each one of the one or more charging bays which is unique to the charger and is configured to communicate information to the communication device of the portable gas detection instrument when the portable gas detection instrument is docked in the associated one of the one or more charging bays.

In a number of embodiments, data is communicated to the management system from the gas monitoring system via the communication system of the portable gas detection instruments. The communication system of each of the portable gas detection instruments may, for example, communicate with the management system via cellular connectivity. In a number of embodiments, the communication device of each of the portable gas detection instruments include an RFID reader, the cooperating communication device of each of the chargers comprises an RFID tag, and each of the plurality of identifying communication devices comprises and RFID tag.

The present devices, systems, and methods, along with the attributes and attendant advantages thereof, will best be appreciated and understood in view of the following detailed description taken in conjunction with the accompanying drawings.

DETAILED DESCRIPTION

Figure 1:
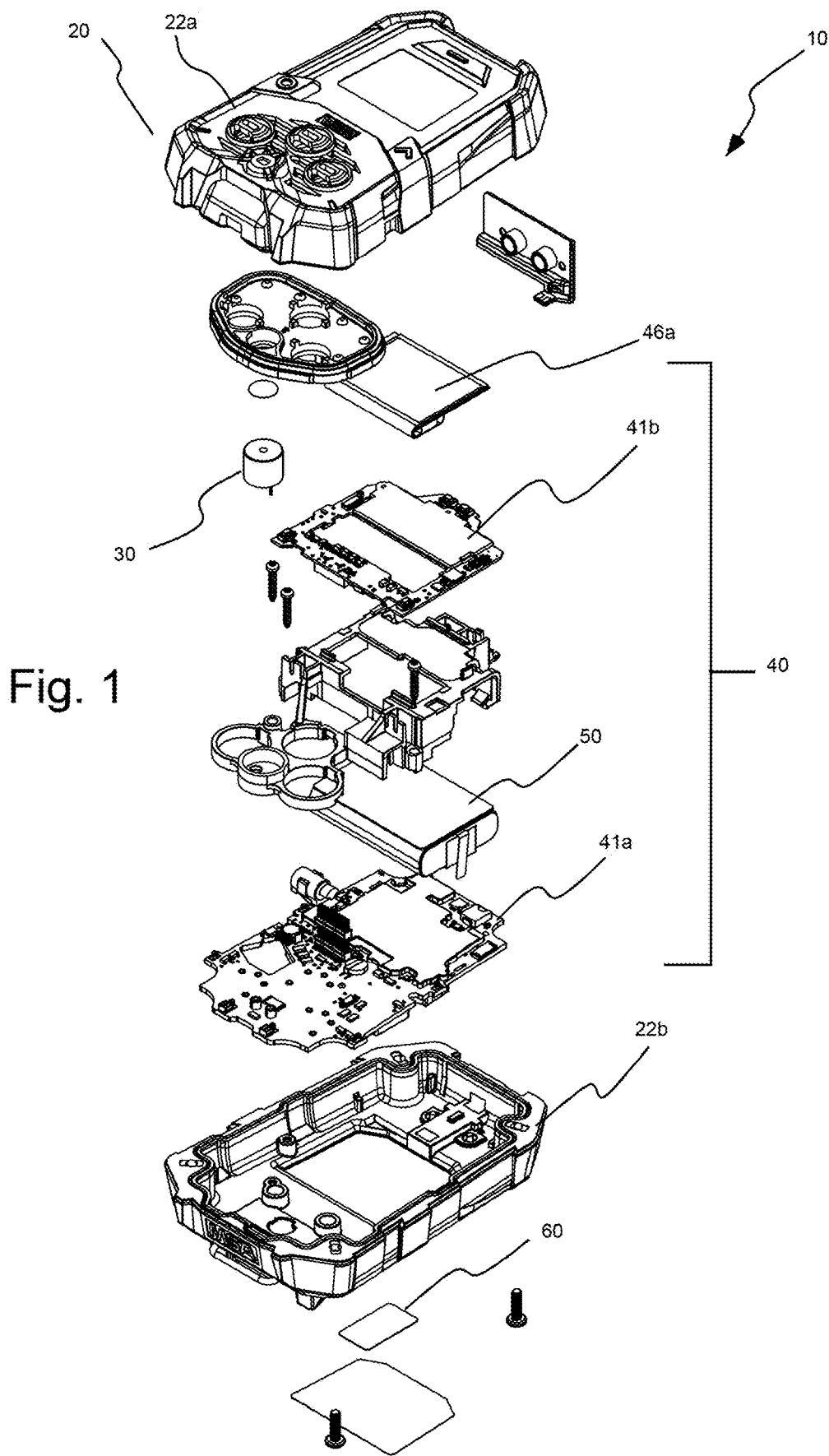
FIG. 1 illustrates an isometric, exploded or disassembled view of an embodiment of a portable gas detection instrument or device hereof.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a charger" includes a plurality of such chargers and equivalents thereof known to those skilled in the art, and so forth, and reference to "the charger" is a reference to one or more such chargers and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software, or combinations of each to perform a function(s) or an action(s). For example, based on a desired feature or need. a circuit may include a software-controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software-controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "logic," as used herein includes, but is not limited to. hardware, firmware, software, or combinations thereof to perform a function(s) or an action(s), or to cause a function or action from another element or component. Based on a certain application or need, logic may, for example, include a software controlled microprocess, discrete logic such as an application specific integrated circuit (ASIC), or other programmed logic device. Logic may also be fully embodied as software. As used herein, the term "logic" is considered synonymous with the term "circuit."

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

As used herein, the term "personal communications device" refers to a portable or mobile device which includes a communication system, a processor system, a user interface system (for example, a visual feedback system including a touchscreen or other display, an auditory feedback system, and a tactile feedback system, a user input system etc.) and an operating system capable of running general-purpose applications. Examples of personal communications devices include, but are not limited to, smartphones, tablet computer and custom devices. As used herein, the term "tablet computer" or tablet, refers to a mobile computer with a communication system, a processor system, at least one user interface as described above (typically including a touchscreen display), and an operating system capable of running general-purpose applications in a single unit. As used herein, the term "smartphone" refers to a cellular telephone including a processor system, at least one user interface as described above (typically including a touchscreen display), and an operating system capable of running general-purpose applications. Such personal communication devices are typically powered by rechargeable batteries and are housed as a single, mobile unit. Moreover, in a number of embodiments personal communications devices are able accept input directly into a touchscreen (as opposed to requiring a keyboard and/or a mouse). Personal communications devices as typically provide for internet access through cellular networks and/or wireless internet access points connected to routers. A number of representative embodiments of systems and/or methods hereof are discussed in connection with the user of a smartphone as the personal communication device.

As used herein, the term "database" refers an organized collection of structured information, or data, typically stored electronically in a memory system of a computer system.

A number of accessories are required for the use and maintenance of portable gas detection instruments of a gas monitoring system of an entity (for example, a company or facility). For example, a charger or charging unit is required to recharge the battery system of portable gas detection instruments. Chargers for portable gas detection instruments may, for example, include a single or multiple bays for charging a single or multiple instruments. Portable gas detection instruments are typically placed on charge at the end of each shift/use.

Moreover, periodic calibration of gas detection instruments is required for continued operation. In that regard, prudence dictates that all gas detection instruments be tested regularly for functionality. It is a common practice to, for example, perform a "bump check," or functionality check on portable gas detection instrumentation periodically. The purpose of this test is to ensure the functionality of the entire gas detection instrument. A periodic bump check or functionality check may extend the period between full calibrations. A bump check typically includes: a) applying a gas of interest (usually a gas having a known concentration of the gas the instrument is intended to detect or a simulant therefor); b) collecting and interpreting the sensor response; and c) indicating to the end user the functional state of the system (that is, whether or not the instrument is properly functioning). Such bump tests are performed regularly and, often, daily. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is being interpreted properly. Moreover, the bump check ensures that the indicator(s) or user interface(s) (for example, a display and/or an annunciation functionality) of the gas detection instrument is/are functioning as intended.

Recently, electronic, and other tests that do not require the application of a calibration or test gas to a gas detection instrument have been developed to test instrument sensors, electronics, and/or transport paths. See, for example, U.S. Pat. Nos. 9,410,940, 9,562,873, 9,528,957, 9,784,755, 10,234,417, 10,578,573, 10,627,379, 10,788,457, 10,788, 458, 10,908,111, 10,948,469, and 10,983,103 and US Patent Application Publication Nos. 2020/0103387, 2020/0363306, 2020/0393405 and 2021/0181135, the disclosures of which are incorporated herein by reference. Such tests may, for example, extend the period of time required between bump tests and/or full calibrations.

Figure 3:
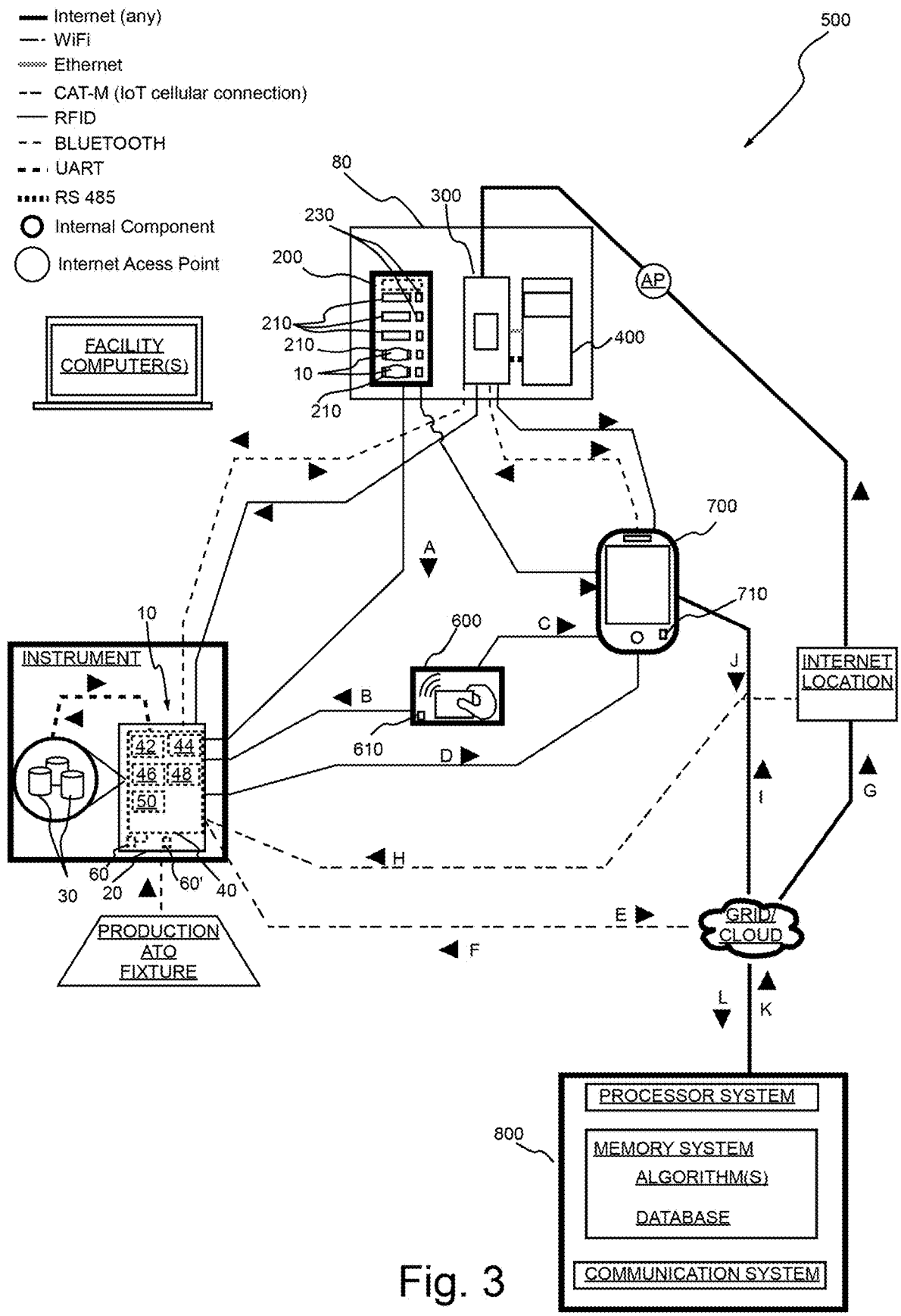
FIG. 3 illustrates an embodiment of a system or grid hereof which provides for communication between a facility's gas monitoring system (including gas detection instruments and accessories therefor) and a supervisory or management system/application for real-time notifications, instrument configuration, fleet management, relevant contextual reporting, instrument assignment/de-assignment, etc.

FIGS. 1 and 3 illustrates an embodiment of a portable instrument or device 10 including a housing 20 formed from housing sections 22a and 22b to encompass one or more sensors 30, each of which is operable to detect the presence of an analyte, and electronic circuitry 40 including a controller or control system to control operation of sensor 10 and to analyze or interpret the responses of the sensor(s) 30. As illustrated schematically in FIG. 3, the control system may, for example, include a processor system 42 (for example, including one or more microprocessors) in operative connection with a memory system 44. As illustrated in FIG. 1, elements of electronic circuitry can be incorporated in one or more printed circuit boards 41a and 41b. One or more software algorithms may be stored in memory system 44 which is/are executable by processor system 42 to control/operate instrument 10 including, for example, data measurement/acquisition, analysis, communication etc. A user interface system 46 (including, for example, a display 46a (see FIGS. 1 and 3), a speaker, a tactile system, etc.) may also be placed in operative or communicative connection with processor system 42. A communication system 48 is in operative or communicative connection with processor system 42 for wired and/or wireless communication to other devices/systems. A power source 50 (for example, a battery system including one or more lithium batteries) provides power for electronic circuitry 40. Gas sensor(s) 30 may, for example, be placed in operative or communicative connection with electronic circuitry 40 via Universal Asynchronous Receive/Transmitter or UART protocol which may, for example, be a part of integrated circuit (IC) used for serial communications over a serial port.

FIGS. 2A through 2D illustrate an embodiment of a multiple-unit charger 200 via which power source/battery 50 of one or more instruments 10 is charged. As illustrated schematically in FIG. 3, a gas detection system 500 hereof (which includes one or more instruments 10 and single-unit and/or multi-unit chargers 200 hereof) may, for example, further include a calibration stand 300, a gas cylinder holder 400, and one or more gas sensing instruments 10. Calibration stands 300 and gas cylinder holders 400 are, for example, described in U.S. Pat. No. 7,530,255.

In a number of embodiments hereof, a software-based is provided to assist in managing a fleet of gas detection instruments 10 and accessories therefor. Such a software-based system or grid may, for example, be implemented on one or more computers located at a facility or located remotely. In a number of embodiments, the software-based management system or grid is a cloud-based system. For example, management system hereof is a cloud-based system via which a particular facility may create an account to enable use of the software-based management system to assist the facility in consolidating and streamlining gas detection related activities in a single source, thereby facilitating information access, instrument/accessory compliance, risk assessment, and worker compliance. A cloud-based system may also facilitate sharing of information or data with a remote location (for example, of a manufacturer of gas detection instruments and accessories therefor) to, for example, further process data and/or provide enhanced functionality.

An area in which further development is desirable is the tracking, maintaining, and controlling of a facility's portable gas detection instruments and accessories therefor and, particularly, the return/de-assignment and removal/assignment into use of portable gas detection instruments. As described above, under current procedures a facility or company typically uses paper records to assign a particular instrument when placed in use with a user/worker at the beginning of a shift and to return/de-assign that instrument at the end of the shift. In a number of more mature implementations, information is manually entered in a dedicated software system. Under current practices, data generated by an instrument during use thereof is not typically associated with a particular user or worker, either in real-time or historically. In a number of embodiments, devices, systems, and methods hereof automate assignment and/or return/de-assignment processes. Further, devices, systems, and methods hereof may readily be used to assign or associated a device/instrument (and data points associated with use of that device/instrument) to a particular user/worker in an automated manner over a period or periods of time when a particular portable gas detection instrument is assigned to the particular user/worker (as determined by an automated assignment and return/de-assignment methodology hereof).

In a number of embodiments hereof, a software-based management system is placed in communicative connection with the gas monitoring system of an entity. Electronic communication between gas instruments and chargers for such portable gas detection instruments of a particular entity is used to automate an assignment/de-assignment procedure via the management system for each of the portable gas detection instruments of the entity.

FIG. 3 illustrates an embodiment of a gas monitoring system 500 hereof of an entity including portable gas detection instrument(s) 10 as well as accessories therefor. In the illustrated embodiment, system 500 includes an accessory system 80 including one or more single- and/or multiple-unit chargers 200, calibration stands 300, and gas cylinder holders 400 to operatively connect to gas cylinders. Various wired and/or wireless communication protocols as illustrated in FIG. 3 may be used in system 500 to communicate data between devices and to a supervisory or management system 800 including one or more processor systems programmed with one or more algorithms stored in a memory system as, for example, described herein.

Figure 4:
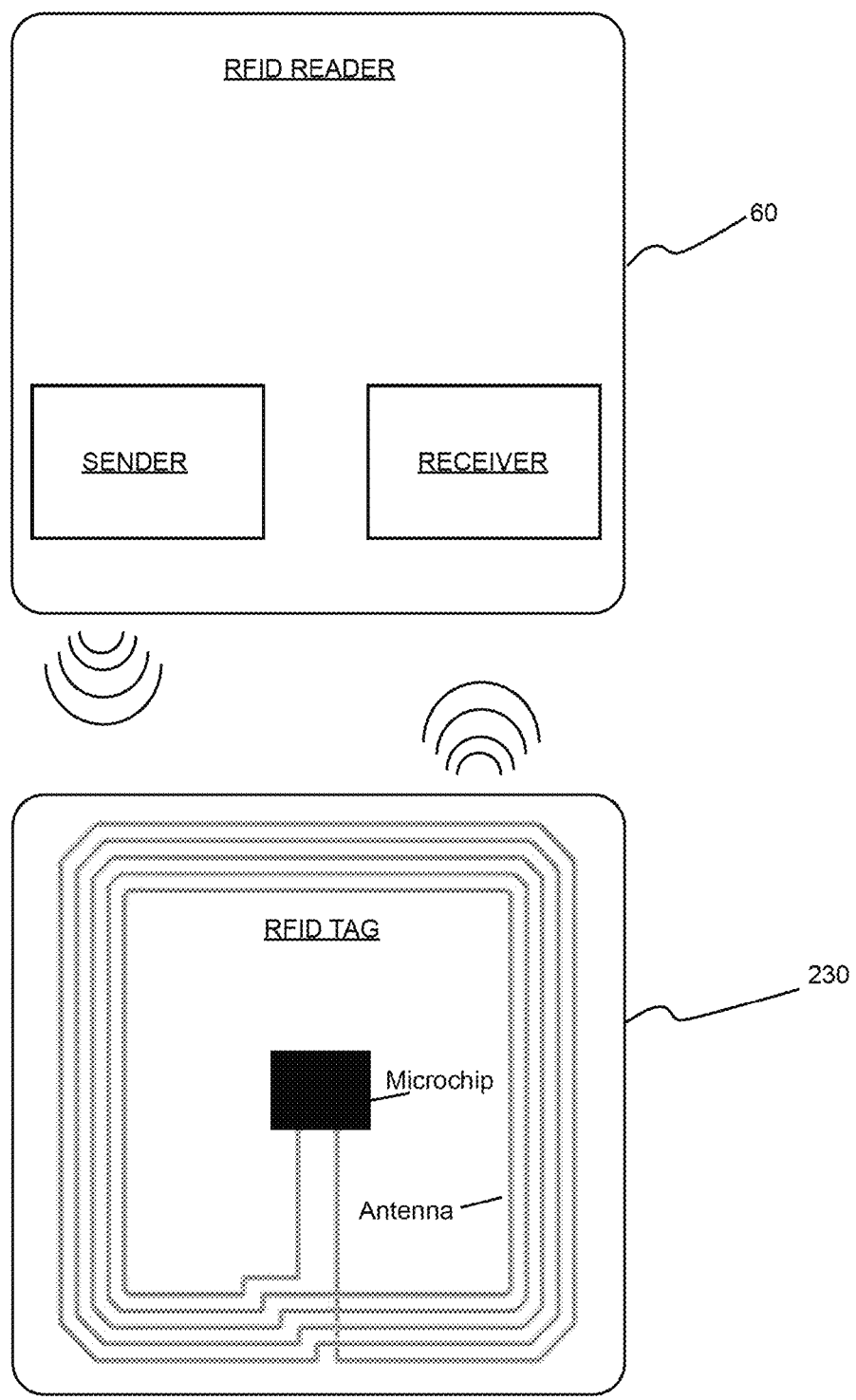
FIG. 4 illustrates schematically communication of information via electromagnetic energy (radio frequency energy) between a communication device such as an RFID tag and a cooperating communication device such as an RFID reader.

In the illustrated embodiment, portable gas detection instrument 10 includes a one or more communication devices which are operable to or configured to communicate data/information to/from an associated memory. Such a communication device may, for example, be integrated into or be in operative/communicative connection with communication system 48 and/or electronic circuitry 40. The communication device or devices communicate with a corresponding communication device in multi-unit charger 200 upon docking of instrument 10 in one of charging bays 210 thereof. In that regard, the proximity of the communication device of instrument 10 and the corresponding communication device of charger bay 210 may initiate communication/transmission of information without user intervention beyond taking some action to effect the docking. The communication device(s) of instrument 10 may communicate with the corresponding communication device of multi-unit charger 200 via a wired (for example, through contact of one or more conductive contact elements) or a wireless manner (for example, via electromagnetic waves such as radio waves). Examples of wireless communication devices suitable for use herein include, but are not limited to, radio-frequency identification (RFID) devices and near field communication (NFC) devices. In a number of embodiments, the communication device of instrument 10 includes an RFID device, reader, or chip 60 which is in operative or communicative connection with electronic circuitry 40. As known in the art and as illustrated schematically in FIG. 4, RFID systems utilize electromagnetic energy/fields to wirelessly communicate with RFID tags which are associated with objects. RFID tags include a microchip or integrated circuit to store and process information. The integrated circuit further modulates and demodulates radio-frequency or RF signals. The RFID tag further includes an antenna to receive and transmit the signal over relatively short distances. Data/information of the tag is stored in a non-volatile memory. Either fixed or programmable logic is provided for processing the transmission and sensor data.

Figure 2A:
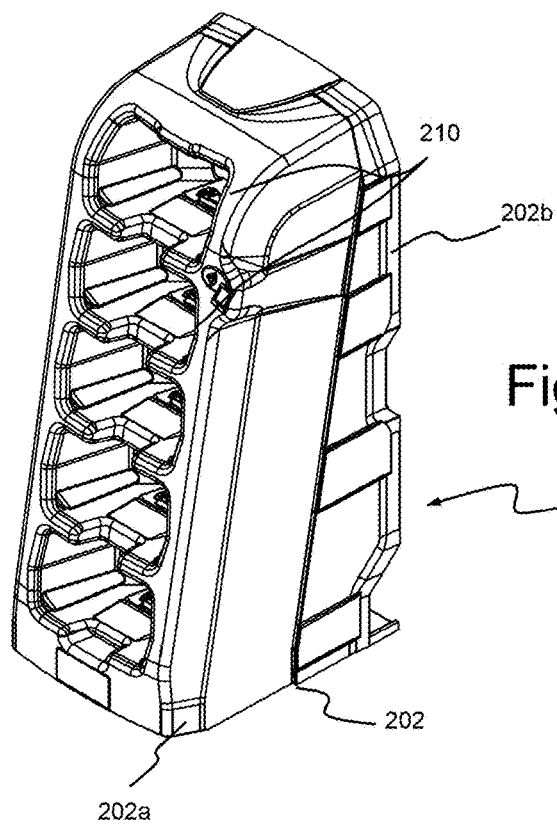
FIG. 2A illustrates an isometric view of an embodiment of a multi-unit charger hereof which is in an empty or non-use state.
Figure 2B:
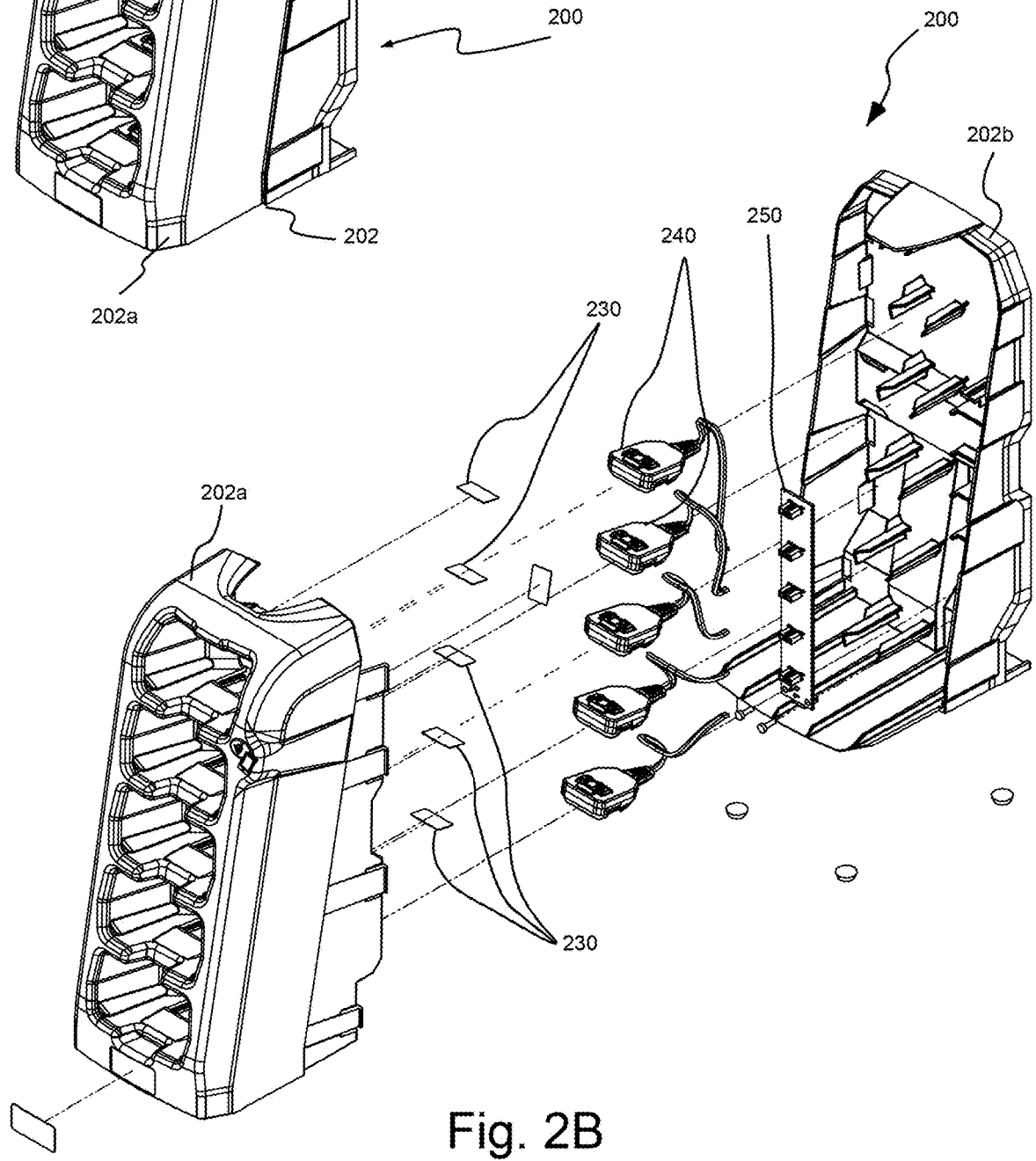
FIG. 2B illustrates an isometric, exploded or disassembled view of the multi-unit charger of FIG. 2A.
Figure 2D:
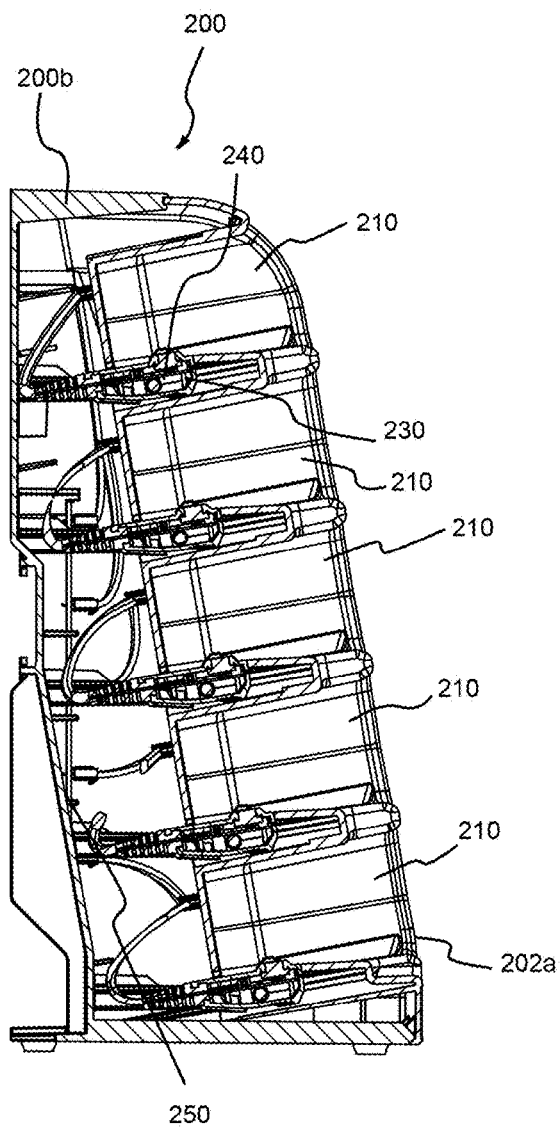
FIG. 2D illustrates a cross-sectional view of the multi-unit charger of FIG. 2A along section B-B of FIG. 2C.
Figure 2C:
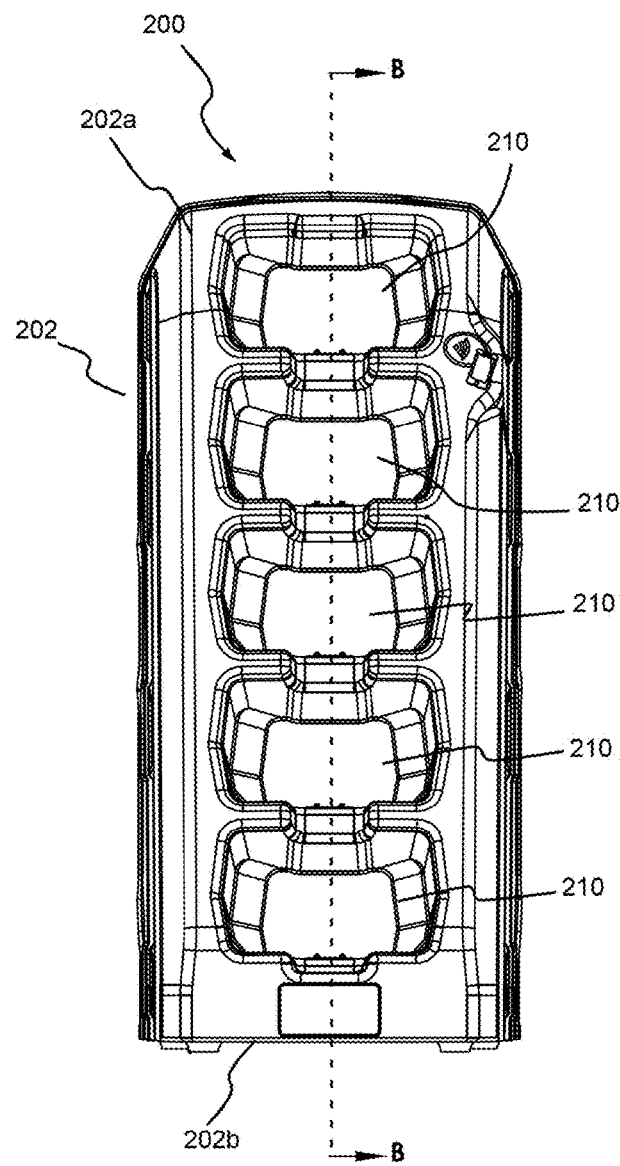
FIG. 2C illustrates a front view of the multi-unit charger of FIG. 2A.

In the illustrated embodiment of gas monitoring system 500, multi-unit charger 200 includes a housing 202 in which five charging bays 210 are formed. In the illustrated embodiment, housing 202 is formed from two housing sections 202a and 202b. A unique RFID device/tag 230 is associated with each bay 210 of charger 200. As illustrated in FIGS. 2B and 2D, a communication device, in the form of an RFID tag 230 in the illustrated embodiment, is positioned adjacent charging coupler 240 which is connected to line power via a printed circuit board 250.

Upon return to one of bays 210, instrument 10 is "digitally returned" and de-assigned from a particular user as described further below. To achieve a seamless return that requires essentially no human intervention, RFID tags 230 in charger 200 are integrated as assets into a database of software-based (for example, a web-application-based) supervisory or management system 800 associated with the entity (for example, a facility or company).

When instrument 10 is inserted in charging bay 210, RFID device 60 communicates with/reads corresponding communication device in the form of charger tag 230. In a number of embodiments, the data transmitted from an RFID tag (or other communication device) of a system hereof includes a universally unique identifier or UUID of the RFID device/tag which is, for example, a 128-bit label used for information in computer systems. The UUID or other unique identifier of charger tag 230 is, for example, associated with the information of charger 200 stored in the database of management system 800, including information identifying charger 200 as an asset of the entity. When the UUID or other unique identifier is transmitted from gas monitoring system 500 to management system 800, one or more algorithms of system 800 are executed by the processor system thereof and a determination is made if charger 200 is an asset of the entity based upon information saved in the database. Thus, the information transmitted by RFID device/reader 60 enables recognition that multi-unit charger 200 is a valid device (that is, not any random charger but a charger that is an asset of the correct entity). Upon a determination that charger 200 is a valid device, instrument 10 is designated as returned by management system 800 (that is, electronically or digitally) and instrument 10 is de-assigned from the user to whom instrument 10 was last assigned. The transfer of data between charger 200 and instrument 10 is illustrated by arrow A in FIG. 3.

In a number of embodiments, instrument 10 can be placed into any charger that is registered to the entity's system/account as an asset of the entity to effect a return/de-assignment. If an instrument were, for example, to be placed into unregistered charger in a number of embodiments, that instrument would not be digitally designated as returned and the instrument would not be de-assigned from the assigned user. Once again, by registering a charger such as multi-unit charger 200 of FIGS. 2A through 2D to an entity's system/account in management system 800, each of RFID tags 230 in charger 200 is associated with that specific entity. When instrument 10 is returned to any charging bay of a registered charger such as charger 200, instrument 10 reads RFID tag 230 of the associated bay 210 in which instrument 10 was docked, seated, or returned and management system 800 de-assigns the user/worker information previously associated with instrument 10 (as discussed further below). System 500 in combination with management system 800 thus ensures that there is a match between the entity system/account to which instrument 10 has been associated and the entity system/account to which charger 200 has been associated and facilitates the assignment/de-assignment process.

As also illustrated in the embodiment of system 500 of FIG. 3, information associated with individual user data can be substantially automatically transferred via for example a card 600 (or other object or item carried on the person of, including worn by, the user) including a communication device such as an RFID device/tag 610. In that regard, individual user data (associated with a user such as identity, entity affiliation etc.) can be transmitted to RFID device/reader 60 of instrument 10 as represented by arrow B in FIG. 3 upon placing card 600 in proximity to RFID reader 60. In a number of embodiments, the data transmitted from tag includes the UUID or other unique identification information of RFID device/tag 610. The UUID or other unique identification information of RFID tag 610 is associated with the information of the individual user in the database of management system 800. In that regard, upon removal of instrument 10 from bay 210 of charger 220 by a user/worker, the user's information is read (for example, from card 600 when in proximity to instrument 10) by instrument 10 and instrument 10 is designated as assigned to the user. Instrument 10 will remain assigned to the user until instrument 10 is placed in one of bays 10 of a validated charger 100 and a de-assignment occurs as described above.

As described above, assignment and de-assignment may be determined/controlled via transmission of an identifier (for example, the universally unique identifier or UUID) of the RFID tags or other communication device associated with instruments 10, chargers 200, card 600, and or other equipment. The identification and/or other information associated with instruments 10, chargers 200 and individual user cards 600 is stored in the software database system of management system 800. For example, upon transmission of the UUID associated with one of RFID tags 230 the cloud-based software system, algorithms of the software check that information against the stored records to determine if a valid assignment or de-assignment tag and may then send the appropriate command(s) back to instrument 10. Those commands include, for example, "instrument xxx is now assigned to John Doe" or 'this "instrument xxx is no longer assigned."

In a typical work cycle of a user, the user may, for example, begin a work period as described above by removing instrument 10 from a charging bay and bringing card 600 into communication with instrument 10, thereby assigning instrument 10 to the user. The user may, for example, then be instructed to dock instrument 10 with a bay 310 of a calibration stand 300 for a bump test. After a successful bump test, the user may proceed with the user's workday with instrument 10 being assigned to the user and monitored by system 500. As described above, at the end of a shift, instrument 10 is returned to a valid charger 200 and is de-assigned from the user.

The robust assignment and return/de-assignment processes provided by system 500 and management system 800 may be used to associate all device/instrument data points (which may be transmitted from instrument 10 to management system 800 either directly or via an intermediate device) to a particular user/worker (when an instrument is assigned to that particular user/worker) without increasing overheard labor. Such data points include, but are not limited to, gas exposure, testing compliance, safety behaviors, and location data. Gas detection instruments and associated accessories are typically shared by multiple users within a facility. Using system 500 in connection with management system 800, one may aggregate all data within a fleet of gas detection instruments around a specific user, rather than around only a specific instrument. In system 500 and the associated methodologies hereof, a user does not need to change the user's workflow to complete the assignment/de-assignment processes described herein. The user simply places instrument 10 into charger bay 210 at the end of the shift as typical and return/de-assignment is automated via system 500. Likewise, assignment is automated upon a user removing instrument 10 from a charger bay 210 at the beginning of a shift.

In a number of embodiments, a lock setting is provided in the software stored in memory system 44 of instrument 10. If such a lock setting is enabled, instrument 10 will not enter a normal operating mode until it is assigned to a validated user. In a number of embodiment, if the lock setting is enabled and instrument 10 is powered on and not currently assigned, it will go into locked state. Once instrument 10 is assigned, it will not enter a locked state at power on until it has been de-assigned via communication with a validated charger 200 or via other means (for example, upon receiving a direct command from management system 800 or from an alternative path). Once instrument 10 reads, for example, RFID tag 610, which has been previously registered in or associated with system 500 of an entity within the database of management system 800, instrument 10 unlocks and enters a normal operating mode. In a number of embodiments, to increase safety, instrument 10 unlocks, for example, upon reading any tag of the ISO 15693 standard and goes into measurement mode upon unlocking. However, if management system 10 determines the read tag to have been an invalid tag, management system 800 may send a repetitive push alert to instrument 10 that an invalid tag has been used to unlock instrument 10, and instrument 10 will not be marked as assigned. At the next power on of instrument 10, instrument 10 will be in the locked state because it wasn't properly assigned. System 500, in connection with management system 800, executes checks to ensure tag assignments are valid. Once again, tags read by RFID device/reader 60 of instrument 10 must be assigned to the same entity system/account to which instrument 10 is assigned (for example, to the system/account of a particular facility).

In addition to transfer of information form card 600 to instrument 10, information can be transferred from card 600 of the user to a personal communication device 700 of the user as represented by arrow C in FIG. 3. Personal communication device 700 may, for example, be a near field communication NFC/RFID enabled device as represented schematically by element 710 in FIG. 3. Furthermore, personal communication device 700 may receive data from instrument 10 via RFID communication from an RFID tag 60' or other communication device of instrument 10 as represented by arrow D. Personal communication device 600 (for example, a smartphone) may, for example, be used in management of RFID tag and associating data with such tags in management system 800. In that regard, an application or app can be downloaded (for example, from management system 800) via which personal communication device 700 can be used to, for example, set up/program RFID tags or other communication devices to, for example, associate personal/identity information or data of the associated user with the UUID of RFID tag 610 or other communication device of card 600. A mobile app on personal communication device 700 may, for example, be used to download a workforce roster from management system 800. Placing personal communication device 700 into proximity with card 600 can be used to achieve pairing, for example, in the cloud.

As illustrated in FIG. 3, devices of system 500 may be connected to a facility network and to the internet/cloud through various wired and/or wireless communication protocols/connections including, for example, ethernet, Wi-Fi, cellular (for example, CAT-M for IoT (internet of things) cellular connection from large numbers of devices), etc. via one or more communication paths. Instrument 10 may, for example, utilize a CAT-M connection to transfer data (represented by arrow E in FIG. 3) such as instrument live data, instrument logs, dock status, cylinder status, instrument configuration updates, and data for assignment/de-assignment. Instrument 10 may, for example, received data (represented by arrow F in FIG. 3) such as instrument configuration, instrument firmware updated commands, alarm updated (for example, evacuation etc.), and assignment/de-assignment data. Instrument 10 may further receive data (via paths represented by arrow G and H) such as an instrument firmware update bundle. In a number of embodiments, all data communicated via the cloud between instrument 10 and management system 800 occurs via cellular/CAT-M or 2G connectivity. If such connectivity is lost, data/information may be stored (for example, on instrument 10) until a cellular connection is reestablished. In other embodiments, redundant communication paths using other connectivity pathways and/or protocols as illustrated in FIG. 3 may be used. Communication of data between personal communication device 700 and the cloud/management system 800 is represented by arrows I and J in FIG. 3.

Management system 800, which may, for example, include a computer or a plurality of interconnected/networked computers, provides a centralized destination for managing/monitoring the facility's fleet of gas detection instruments and accessories therefor. In a number of embodiments, management system 800 is accessible, for example, via account login from facility computers, mobile devices etc. One may, for example, provide real-time notifications, instrument configuration, fleet management and relevant contextual reporting via system/grid. Management system 800 may, for example, execute a web-based application to transmit data to system 500 (represented by arrow K in FIG. 3) and received data (represented by arrow L in FIG. 3) from system 500.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A management system, comprising:
a processor system,
a communication system in operative connection with the processor system and configured to be in communicative connection with a gas monitoring system of an entity, the gas monitoring system including one or more portable gas detection instruments, each portable gas detection instrument including one or more gas sensors and a rechargeable battery system, one or more chargers configured to charge the rechargeable battery system of each of the portable gas detection instruments, and a plurality of identifying communication devices, wherein each of the plurality of identifying communication devices is configured to be associated with one of a plurality of users and to be carried-by the one of the plurality of users, and
a memory system in operative connection with the processor system, the memory system comprising an algorithm executable by the processor system stored therein and a database associated with the algorithm stored therein, the database comprising data identifying each of the chargers as an asset of the entity and each of the portable gas detection instruments as an asset of the entity and data identifying the one of the plurality of users associated with each of the plurality of identifying communication devices,
wherein, upon docking of one of the portable gas detection instruments with one of the chargers, communication between the one of the portable gas detection instruments docked and the one of the chargers is initiated and data is communicated to the management system electronically by the gas monitoring system regarding the docking and an identity of the one of the chargers, the processor system of the management system being configured, upon communication of the data regarding the docking and an identity of the one of the chargers from the gas monitoring system to the management system, to execute the algorithm to confirm identification of the one of the chargers as an asset of the entity, and to de-assign the one of the portable gas detection instruments from one of a plurality of users to whom the one of the portable gas detection instruments was previously assigned if one of the chargers is determined to be an asset of the entity, and
wherein, upon removal of one of the portable gas detection instruments from one of the chargers by one of the plurality of users, positioning of the one of the plurality of identifying communication devices associated with the one of the plurality of users in proximity with the one of the portable gas detection instruments, communication between the one of the portable gas detection instruments and the one of the plurality of identifying communication devices associated with the one of the plurality of users is initiated and data regarding the identity of one of the portable gas detection instruments and identity of the one of the plurality of users is communicated to the management system electronically by the gas monitoring system, the processor system of the management system being configured, upon communication of the data regarding the identity of one of the portable gas detection instruments and the identity of the one of the plurality of user from the gas monitoring system to the management system, to execute the algorithm to assign the one of the gas detection instruments to the one of the plurality of users.

2. The management system of claim 1 wherein each of the portable gas detection instruments includes electronic circuitry in operative connection with the rechargeable battery system, a communication system in operative connection with the electronic circuitry, and a communication device in operative connection with the electronic circuitry, and wherein each of the chargers comprises one or more charging bays, wherein each charging bay is configured to recharge the rechargeable battery system of one of the portable gas detection instruments when docked therein, each of the chargers including a separate cooperating communication device associated with each one of the one or more charging bays which is unique to the charger and is configured to communicate information to the communication device of the one of the portable gas detection instruments when the one of the portable gas detection instruments is docked in one of the one or more charging bays.

3. The management system of claim 2 wherein data is communicated to the management system from the gas monitoring system via the communication system of the portable gas detection instruments.

4. The management system of claim 3 wherein the communication system of each of the portable gas detection instruments communicates with the management system via cellular connectivity.

5. The management system of claim 3 wherein the communication device of each of the portable gas detection instruments comprises an RFID reader, the cooperating communication device of each of the chargers comprises an RFID tag, and each of the plurality of identifying communication devices comprises an RFID tag.

6. The management system of claim 3 wherein data transmitted to the management system by the one of the portable gas detection instruments assigned to the one of the plurality of users regarding use of the one of the portable gas detection instruments is associated to the one of the plurality of users until the one of the portable gas detection instruments is de-assigned from the one of the plurality of users by the management system.

7. A method of managing a gas monitoring system of an entity, the gas monitoring system including one or more portable gas detection instruments, each portable gas detection instrument including one or more gas sensors and a rechargeable battery system, one or more chargers configured to charge the rechargeable battery system of each of the portable gas detection instruments, a plurality of identifying communication devices, wherein each of the plurality of identifying communication devices is configured to be associated with one of a plurality of users and to be carried by the one of the plurality of users, comprising:

placing a management system in communicative connection with the gas monitoring system, the management system comprising
a processor system,
a communication system in operative connection with the processor system and configured to be placed in communicative connection with the gas monitoring system of the entity, and
a memory system in operative connection with the processor system, the memory system comprising an algorithm executable by the processor system stored therein and a database associated with the algorithm stored therein, the database comprising data identifying each of the one or more chargers as an asset of the entity and each of the portable gas detection instruments as an asset of the entity and data identifying the one of the plurality of users associated with each of the plurality of identifying communication devices,
upon docking of one of the portable gas detection instruments with one of the chargers, initiating communication between the one of the portable gas detection instruments docked and the one of the chargers,
communicating data from the gas monitoring system to the management system regarding the docking and an identity of the one of the chargers,
upon communication of the data regarding the docking and an identity of the one of the chargers from the gas monitoring system to the management system, the processor system executing the algorithm to confirm identification of the one of the chargers as an asset of the entity and to de-assign the one of the portable gas detection instruments from one of a plurality of users to whom the one of the gas detection instruments was previously assigned if one of the chargers is determined to be an asset of the entity, and
upon removal of one of the portable gas detection instruments from one of the chargers by one of the plurality of users and positioning of the one of the plurality of identifying communication devices associated with the one of the plurality of users in proximity with the one of portable gas detection instruments, communication between the one of the portable gas detection instruments and the one of the plurality of identifying communication devices associated with the one of the plurality of users is initiated and data regarding the identity of one of the portable gas detection instruments and identity of the one of the plurality of users is communicated to the management system electronically by the gas monitoring system, the processor system of the management system being configured, upon communication of the data regarding the identity of one of the portable gas detection instrument and the identity of the one of the plurality of user from the gas monitoring system to the management system, to execute the algorithm to assign the one of the gas detection instruments to the one of a plurality of users.

8. The method of claim 7 wherein each of the portable gas detection instruments includes electronic circuitry in operative connection with the rechargeable battery system, a communication system in operative connection with the electronic circuitry, and a communication device in operative connection with the electronic circuitry, and wherein each of the chargers comprises one or more charging bays, wherein each of the charging bays is configured to recharge the rechargeable battery system of one of the portable gas detection instruments when docked therein, each of the chargers including a separate cooperating communication device associated with each one of the one or more charging bays which is unique to the charger and is configured to communicate information to the communication device of the one of the portable gas detection instruments when the one of the portable gas detection instruments is docked in one of the one or more charging bays.

9. The method of claim 8 wherein data is communicated to the management system from the gas monitoring system via the communication system of the portable gas detection instruments.

10. The method 11 wherein the communication system of each of the portable gas detection instruments communicates with the management system via cellular connectivity.

11. The method of claim 9 wherein the communication device of each of the portable gas detection instruments comprises an RFID reader, the cooperating communication device of each of the chargers comprises an RFID tag, and each of the plurality of identifying communication devices comprises an RFID tag.

12. The method of claim 9 wherein data transmitted to the management system by the one of the portable gas detection instruments assigned to the one of the plurality of users regarding use of the one of the portable gas detection instruments is associated to the one of the plurality of users until the one of the portable gas detection instruments is de-assigned from the one of the plurality of users by the management system.

13. A system, comprising:
a gas monitoring system of an entity comprising:
one or more portable gas detection instruments, each portable gas detection instrument comprising one or more gas sensors and a rechargeable battery system,
one or more chargers configured to charge the rechargeable battery system of each of the portable gas detection instruments, and
a plurality of identifying communication devices, wherein each of the plurality of identifying communication devices is configured to be associated with one of a plurality of users and to be carried by the one of the plurality of users,
a management system comprising
a processor system,
a communication system configured to be in communicative connection with the gas monitoring system of the entity, and
a memory system in operative connection with the processor system, the memory system comprising an algorithm executable by the processor system stored therein and a database associated with the algorithm stored therein, the database comprising data identifying each of the chargers as an asset of an entity and each of the portable gas detection instruments as an asset of the entity and data identifying the one of the plurality of users associated with each of the plurality of identifying communication devices, wherein, upon docking of one of the portable gas detection instruments with one of the chargers, communication between the one of the portable gas detection instruments docked and the one of the chargers is initiated and data is communicated to the management system electronically by the gas monitoring system regarding the docking and an identity of the one of the chargers, the processor system of the management system being configured, upon communication of the data regarding the docking and an identity of the one of the chargers from the gas monitoring system to the management system, to execute the algorithm to confirm identification of the one of the chargers as an asset of the entity, and to de-assign the one of the portable gas detection instruments from one of a plurality of users to whom the one of the portable gas detection instruments was previously assigned if one of the chargers is determined to be an asset of the entity, and wherein, upon removal of one of the portable gas detection instruments from one of the chargers by one of the plurality of users, positioning the one of the plurality of identifying communication devices associated with the one of the plurality of users in proximity with the one of the portable gas detection instruments, communication between the one of the portable gas detection instruments and the one of the plurality of identifying communication devices associated with the one of the plurality of users is initiated and data regarding the identity of one of the portable gas detection instrument and identity of the one of the plurality of users is communicated to the management system electronically by the gas monitoring system, the processor system of the management system being configured, upon communication of the data regarding the identity of the one of the portable gas detection instruments and the identity of the one of the plurality of user from the gas monitoring system to the management system, to execute the algorithm to assign the one of the gas detection instruments to the one of a plurality of users.

14. The system of claim 13 wherein each of the portable gas detection instruments includes electronic circuitry in operative connection with the rechargeable battery system, a communication system in operative connection with the electronic circuitry, and a communication device in operative connection with the electronic circuitry, and wherein each of the chargers comprises one or more charging bays, wherein each of the charging bays is configured to recharge the rechargeable battery system of one of the portable gas detection instruments, each of the chargers including a separate cooperating communication device associated with each one of the one or more charging bays which is unique to the charger and is configured to communicate information to the communication device of the one of the portable gas detection instruments when the one of the portable gas detection instruments is docked in one of the one or more charging bays.

15. The system of claim 14 wherein data is communicated to the management system from the gas monitoring system via the communication system of the portable gas detection instruments.

16. The system of claim 15 wherein the communication system of each of the portable gas detection instruments communicates with the management system via cellular connectivity.

17. The system of claim 15 wherein the communication device of each of the portable gas detection instruments comprises an RFID reader, the cooperating communication device of each of the chargers comprises an RFID tag, and each of the plurality of identifying communication devices comprises an RFID tag.

* * * * *

UNITED STATES PATENT AND TRADEMARK OFFICE
CERTIFICATE OF CORRECTION

PATENT NO. : 12,174,166 B2
APPLICATION NO. : 17/496420
DATED : December 24, 2024
INVENTOR(S) : Chris Borneo, Steve Denninger and Victor Lejeune Page 1 of 1

It is certified that error appears in the above-identified patent and that said Letters Patent is hereby corrected as shown below:

In the Specification

Column 12, Line 58 delete "charger 220" and insert --charger 200--.
Column 12, Line 63 delete "bays 10" and insert --bays 210--.
Column 12, Line 63 delete "charger 100" and insert --charger 200--.
Column 14, Lines 26 and 27 delete "device 600" and insert --device 700--.

In the Claims

Column 18, Line 23 Claim 10, delete "The method 11" and insert --The method of claim 9--.

Signed and Sealed this
Fourth Day of March, 2025

Coke Morgan Stewart
*Acting Director of the United States Patent and Trademark Office*